United States Patent [19]

Mehra et al.

[11] Patent Number: 4,993,263

[45] Date of Patent: Feb. 19, 1991

[54] PLASTIC HYDROMETER

[75] Inventors: Ravinder C. Mehra, Fairport; Paul V. Comeau, Macedon, both of N.Y.

[73] Assignee: Nalge Company, Rochester, N.Y.

[21] Appl. No.: 354,014

[22] Filed: May 19, 1989

[51] Int. Cl.$^5$ ............................................... G01N 9/12
[52] U.S. Cl. .................................................... 73/448
[58] Field of Search .................. 73/448, 449, 444, 441

[56] References Cited

U.S. PATENT DOCUMENTS

| 1,972,220 | 9/1934 | Edelmann | 73/448 |
| 2,221,913 | 11/1940 | Edelmann | 73/448 |
| 3,055,220 | 9/1962 | Ryan et al. | 73/448 |

Primary Examiner—John Chapman
Attorney, Agent, or Firm—Marjama & Pincelli

[57] ABSTRACT

A plastic hydrometer of the constant mass variable displacement type. The hydrometer includes a separate bulbous section, stem and cap. The bulbous section is a single piece molded part having an upper end which mates with the lower end of the extruded tube.

13 Claims, 2 Drawing Sheets

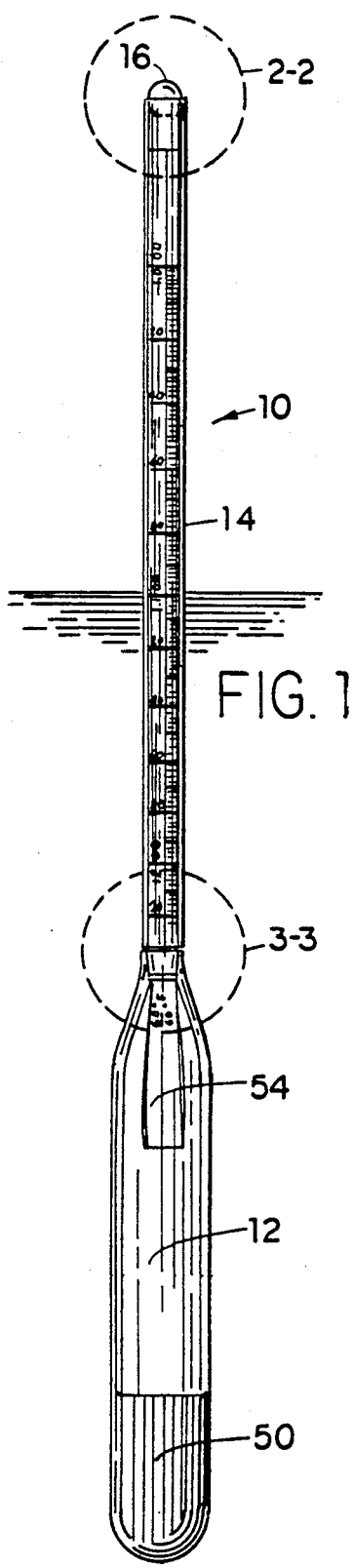
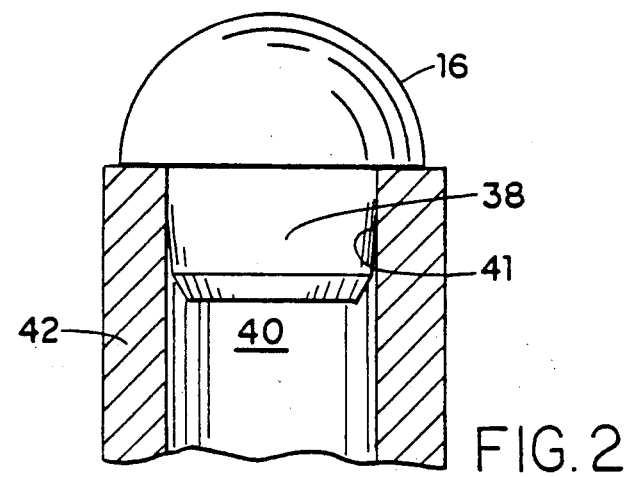
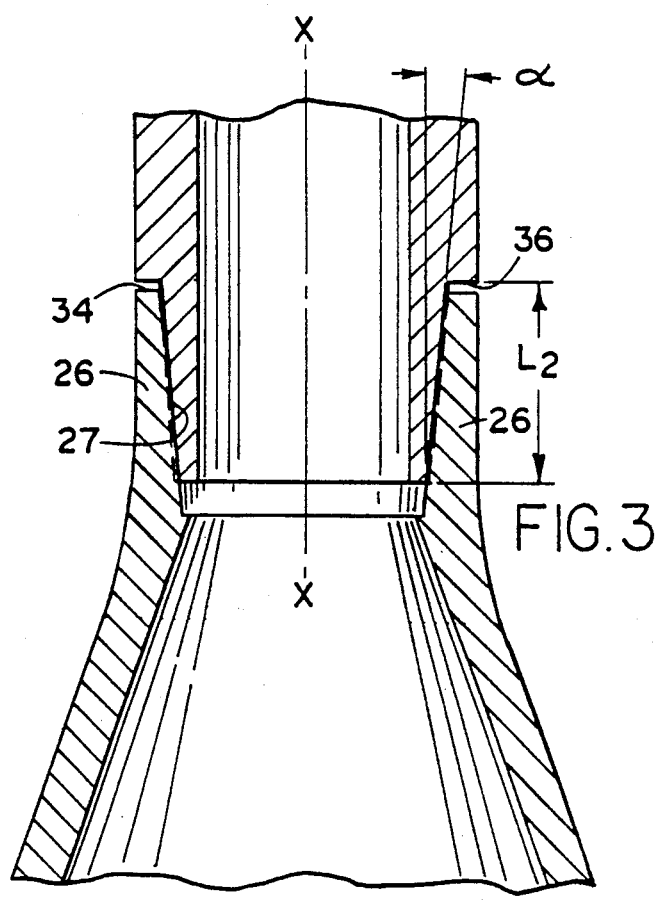

PLASTIC HYDROMETER

FIELD OF THE INVENTION

The present invention is directed to plastic hydrometers and, in particular, hydrometers of the constant mass, variable-displacement type.

BACKGROUND OF THE INVENTION

In the prior art, constant mass, variable-displacement hydrometers have been made of glass. These hydrometers typically comprise a body having a lower ballast section, which usually has a weight secured therein for weighting of the hydrometer, and a stem portion that is integrally formed with the ballast. Typically a paper scale is placed within the stem for providing a direct readout of density. These hydrometers are used by simply placing them in the liquid in which it is to be used, and depending upon the amount which the hydrometer extends into the liquid, an appropriate density can be read off the stem of the device. In these type devices it is important that the outer surface be smooth, transparent, and free of bubbles, striae, or other imperfections that might interfere with the use of the hydrometer. Additionally, these hydrometers should be made of a material that will not react with the chemicals in which it is to be used or exposed, and also have suitable thermal properties to permit its use over a wide range of temperatures. Further, it is also important in these type hydrometers that there be no uneven or unnecessary thickness of the walls, and no abrupt changes or constrictions that would hinder cleaning or tend to trap air bubbles when the instrument is immerged. Because of these high constraints, hydrometers of the prior art have been made of glass. However, these hydrometers, since they are made of glass, are highly subject to breakage.

The present invention concerns an improved plastic hydrometer and method of making same which can provide the stringent requirements required of a constant mass, variable-displacement type hydrometer which is considerably less subject to breakage.

SUMMARY OF THE INVENTION

In one aspect of the present invention there is provided a sealed constant mass plastic hydrometer having an elongated bulbous section, a generally cylindrical stem and end cap. The bulbous section has an upper end which is second to the lower end of the stem. The end cap is secured to the upper end of the stem.

In another aspect of the present invention, there is provided a method of making a sealed constant mass plastic hydrometer having an elongated bulbous section, a generally cylindrical stem and end cap, comprising the steps of:
(a) providing said elongated bulbous section with an upper end which terminates in a mating end;
(b) providing said lower mating end of said stem with a lower mating surface for engagement with said upper mating end of said bulbous section by securing said stems to said elongated bulbous section;
(c) providing means for reading of density from said hydrometer; and
(d) providing an end cap for placement with said upper end of said stem and securing said end cap thereto.

DESCRIPTION OF THE DRAWINGS

FIG. 1 illustrates a front elevational view of a hydrometer made in accordance with the present invention as immersed a liquid;

FIG. 2 is a greatly enlarged cross-sectional view of the outer stem of the hydrometer of FIG. 1 indicated by dash lines 2—2;

FIG. 3 is a greatly enlarged view of a portion of the hydrometer of FIG. 1 illustrated indicated by dash lines 3—3 illustrating how the stem is connected to the ballast section of the hydrometer.

DETAILED DESCRIPTION

Figure 4:
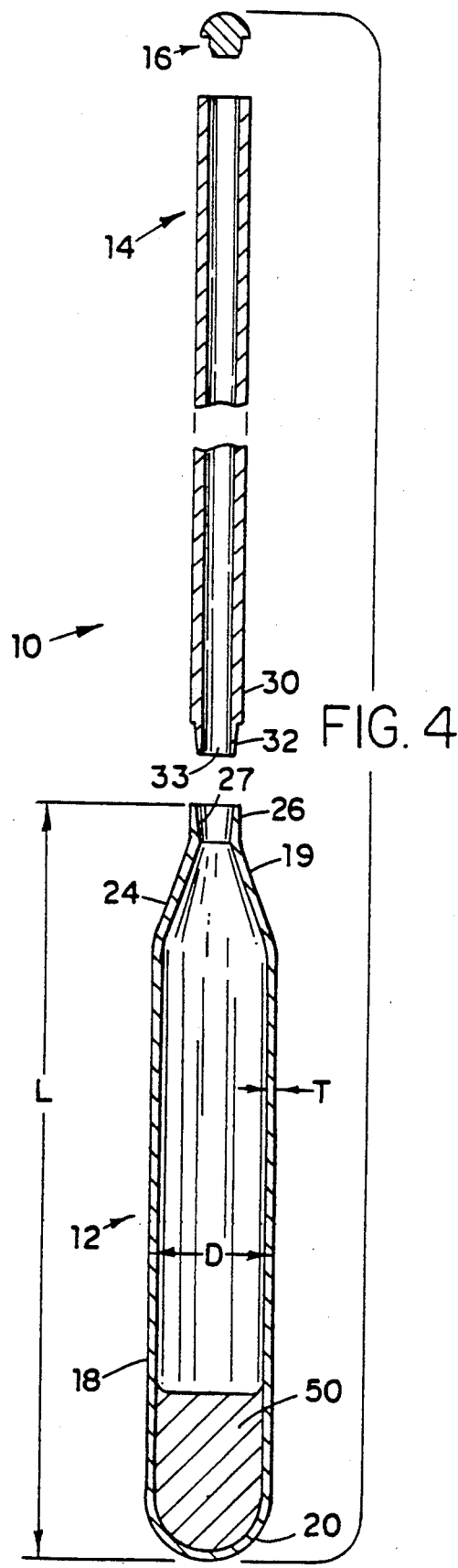
FIG. 4 is an exploded cross-sectional view of the device of FIG. 1.

Referring to FIGS. 1-4, there is illustrated a hydrometer 10 of the constant mass type. The hydrometer 10 is made of a plastic material and comprises an elongated bulbous section 12, a stem 14 and an end cap 16. The bulbous section 12 comprises a generally cylindrical central section 18 having a bottom end 20 and opposite disposed top end 19. Bottom end 20 is integrally formed with central sections 18 and in the particular embodiment illustrated is substantially semi-hemispherical in shape. Top end 19 is also integrally formed with central section 18 and narrows down to a connecting section 26 for mating with stem 14. Preferably as illustrated connecting section 26 has a generally cylindrical tapered seat 27 which forms an angle $\alpha$ with respect to the longitudinal axis x—x of the bulbous section 12 in the range of about 0° to 5°. In the particular embodiment illustrated, the angle $\alpha$ is approximately 3°.

It is important that the elongated bulbous section 12 have a high degree of clarity, a smooth outer surface, and a substantially uniform wall cross-section. For this particular reason it has been found that the bulbous section 12 preferably be injection blow molded so as to provide a high degree of clarity, a smooth outer surface and substantially uniform wall thickness along the length thereof. Injection blow molding techniques are well known in the art and will not be discussed further. In the particular embodiment illustrated, the bulbous section has a length L, a diameter D, and a wall thickness T. The length L of the particular embodiment illustrated is approximately 4 inches, the diameter D is approximately ¾ inch and the thickness t is about 0.1 inch. The material from which the elongated bulbous section 12 is made is polycarbonate. It is to be understood that elongated bulbous section 12 may be made of any desired plastic capable of obtaining the desired properties.

The elongated stem 14 has a lower mating end 30 which has a mating contact surface 32 designed to mate with seat 27 of the elongated bulbous section 12. Contact surface 32 preferably, as illustrated, is disposed at the same angle seat 27 as illustrated. The stem comprise a generally cylindrical tube having a longitudinal extending opening 33. Preferably stem 14 is extruded. In the embodiment illustrated, stem 14 is made of the same plastic material as bulbous section 12. However, here too, the stem may be of any desired plastic material. The mating surface 32 preferably has a length L2 such that a small space is preferably formed between the terminal end 34 of seat 27 and terminal end 36 of stem 14 adjacent thereto. This allows the tapered contact surface 32 to fully engage tapered seat 27. The two parts are preferably secured together by an appropriate adhesive which not only secures the two parts together, but provides an air tight seal between the elongated bulbous section 12 and stem 14. The upper end 36 of stem 14 is sealed with a plastic cap 16 which has an insert section 38 that is designed to fit within the opening 33 such that the outer surface of insert 38 engages the inside surface 41 of stem 14. Cap 16 may be made of any desirable plastic, preferably of the same material stem 14 and bulbous section 12. The end cap 16 is preferably sealed to stem 40 by an appropriate adhesive so as to provide an air tight seal between the two parts. Thus, when fully assembled, the hydrometer 10 provides a sealed inner chamber. In the embodiment illustrated cap 16 fits with stem 14. However, it is to be understood that end cap form may take any other form desired that will provide a sealing relationship.

In the actual assembly of the device, after bulbous section 12 has been formed, an appropriate weight 50 is placed in the bottom portion thereof. Generally, as is typically in the prior art, weight 50 comprises plurality of steel balls that are cemented in place. An appropriate amount of steel balls are inserted into bulbous section 12 and cemented in place so as to properly calibrate the hydrometer. Also, as shown in FIG. 1, there is provided a paper scale that is secured to the inside of stem 14. In the particular embodiment illustrated, the scale 54 is secured by an appropriate adhesive. The paper scale 54 has the appropriate markings thereon to indicate the density as is typically done in such prior art devices.

In the method of making the hydrometer 10, as previously noted, the bulbous section 12 is preferably injection blow molded. However, it is to be understood that the bulbous section 14 may be made by other manufacturing techniques. It has been found that injection blow molding is preferred due to its ability to maintain a uniform thickness and a smooth outer surface to the bulbous section. This is particularly important with regard to constant mass hydrometers of the present invention. The connecting section 26 and seat 27 are integrally formed as a part of bulbous section 12 during molding. The stem 14 is formed by extrusion and is cut to the appropriate length. The lower end 30 is appropriately machined to provide mating contact surface 32 which will mate with the seat 27. Thereafter, an appropriate adhesive is provided between mating surface 32 and seat 22 and placed together into mating engagement. Weight 50 is then added to the elongated bulbous section 12 so as to appropriate calibrate the hydrometer. An appropriate scale 54 is then inserted within the stem 14 and secured thereto, generally by an appropriate adhesive. Thereafter, an end cap 16 is inserted into stem 14 and secured thereto also by any appropriate adhesive. When fully assembled a high durable hydrometer is produced which is highly resistant to breakage yet provides the necessary requirements for a constant mass, variable-displacement hydrometer.

It is to be understood that various modifications and changes will be made without departing from the scope of the present invention. For example, but not by way of limitation, various other methods may be used to secure the stem to the bulbous section and end cap, for example, ultrasonic welding. Additionally, the stem may be designed to fit around the outside of connecting portion 26. Further, the size and shape of the stem and bulbous section may be varied accordingly so as to provide the desired scale range of a device. For example, by simply varying the diameter of stem 14 different scale ranges may be obtained. The present invention being limited by the following claims.

We claim:

1. A sealed constant mass plastic hydrometer comprising:

an elongated plastic bulbous section, having an upper end and a lower closed end, said upper end terminating in an upper mating end, said upper end includes an annular conical seat;

a generally cylindrical plastic stem having an upper end and a lower end, said lower end of said stem having a lower mating section for mating engagement and attachment with said upper mating end of said bulbous section, said lower end of said stem having a contact mating surface mating engagement with said conical seat; and an end cap for engagement with said upper end of said stem and for providing sealing engagement therewith.

2. A sealed constant mass plastic hydrometer according to claim 1 wherein an adhesive is applied between said contact mating surface and said seat for securing said stem and bulbous section together.

3. A sealed constant mass plastic hydrometer according to claim 1 wherein said annular conical seat has a sealing surface which forms an angle with respect to the longitudinal axis of said hydrometer in the range of 0° to 5°.

4. A sealed constant mass plastic hydrometer according to claim 3 wherein said seat is disposed at an angle of about 3°.

5. A sealed constant mass plastic hydrometer according to claim 3 wherein said contact mating surface is disposed at an angle substantially equal to said sealing surface of said seat.

6. A sealed constant mass plastic hydrometer according to claim 1 wherein said lower closed end of said bulbous section has a substantially semi-hemispherical configuration.

7. A sealed constant mass plastic hydrometer according to claim 1 wherein said end cap fits within said stem.

8. A sealed constant mass plastic hydrometer according to claim 1 wherein said bulbous section is injection blow molded.

9. A sealed constant mass plastic hydrometer according to claim 1 wherein a weight is disposed within said bulbous section.

10. A sealed constant mass plastic hydrometer according to claim 1 wherein a scale is disposed within said stem for determining density of a liquid in which said hydrometer is placed.

11. A sealed constant mass plastic hydrometer comprising:

an injection blow molded elongated plastic bulbous section, said bulbous section having an upper end and a closed lower end, said upper end having an annular conical seat, said conical seat being tapered at an angle up to about 5° with respect to longitudinal axis of said hydrometer;

a cylindrical stem having an upper end and a lower end, said lower end of said plastic stem having an outer mating surface for mating engagement and attachment with said seat in said bulbous section, said mating surface being tapered at the same angle at which said conical seat is tapered;

and end cap for placement in said upper end of stem for providing sealing engagement therewith; and a scale disposed within said stem having means for indicating density.

12. A sealed constant mass plastic hydrometer according to claim 11 wherein a weight is disposed in said bulbous section.

13. A sealed constant mass plastic hydrometer comprising:

an elongated plastic bulbous section having an upper end and a lower closed end, said upper end terminating in an upper mating end, said upper mating end includes a generally annular conical seat disposed at an angle with respect to the longitudinal axis of said hydrometer greater than 0°;

a generally cylindrical plastic stem having an upper and a lower end, said lower end of said stem having a lower mating section for mating engagement and attachment with said seat of said of upper mating end, said lower mating section being disposed at approximately the same angle as said conical seat; and an end cap for engagement with said upper end of said stem and for providing sealing engagement therewith.

* * * * *